United States Patent
Afshar et al.

(10) Patent No.: US 10,820,819 B2
(45) Date of Patent: *Nov. 3, 2020

(54) MOVEMENT DISORDER SYMPTOM CONTROL

(71) Applicant: Medtronic, Inc., Minneapolis, MN (US)

(72) Inventors: Pedram Afshar, San Francisco, CA (US); Timothy J. Denison, Minneapolis, MN (US); David E. Linde, Corcoran, MN (US); Scott R. Stanslaski, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 142 days.

This patent is subject to a terminal disclaimer.

(21) Appl. No.: 16/023,508

(22) Filed: Jun. 29, 2018

(65) Prior Publication Data

US 2018/0304082 A1  Oct. 25, 2018

Related U.S. Application Data

(63) Continuation of application No. 14/599,126, filed on Jan. 16, 2015, now Pat. No. 10,016,606.
(Continued)

(51) Int. Cl.
*A61B 5/00* (2006.01)
*A61B 5/04* (2006.01)
(Continued)

(52) U.S. Cl.
CPC ........ *A61B 5/04012* (2013.01); *A61B 5/0478* (2013.01); *A61B 5/4082* (2013.01);
(Continued)

(58) Field of Classification Search
CPC .............. A61N 1/0534; A61N 1/36067; A61N 1/36135; A61N 1/36139; A61N 1/36171;
(Continued)

(56) References Cited

U.S. PATENT DOCUMENTS

| 5,593,431 A | 1/1997 | Sheldon |
| 6,463,328 B1 | 10/2002 | John |

(Continued)

FOREIGN PATENT DOCUMENTS

| WO | 2013123112 A1 | 8/2013 |
| WO | 2015109239 A1 | 7/2015 |

OTHER PUBLICATIONS

"MDS-UPDRS" Movement Disorder Society, Jul. 1, 2008, 32 pp.
(Continued)

*Primary Examiner* — Eugene T Wu
(74) *Attorney, Agent, or Firm* — Schumaker & Sieffert, P.A.

(57) ABSTRACT

The disclosure describes a method and system or controlling symptoms of patients suffering from Parkinson's Disease. In some examples, one or more biomarkers indicative of a patient's present symptoms are determined. The biomarkers may be used to control therapy delivered to the patient in a closed-loop manner. In addition, biomarkers may be used as an indication of therapy effectiveness.

21 Claims, 10 Drawing Sheets

Related U.S. Application Data

(60) Provisional application No. 61/928,859, filed on Jan. 17, 2014.

(51) Int. Cl.

| | | |
|---|---|---|
| *A61B 5/0478* | (2006.01) | |
| *A61N 1/36* | (2006.01) | |
| *G06F 19/00* | (2018.01) | |
| *G16H 20/40* | (2018.01) | |
| *G16H 50/20* | (2018.01) | |
| *A61N 1/05* | (2006.01) | |

(52) U.S. Cl.
CPC ............ *A61B 5/4836* (2013.01); *A61B 5/686* (2013.01); *A61N 1/36067* (2013.01); *A61N 1/36139* (2013.01); *A61N 1/36171* (2013.01); *G06F 19/00* (2013.01); *G06F 19/3481* (2013.01); *G16H 20/40* (2018.01); *G16H 50/20* (2018.01); *A61N 1/0534* (2013.01)

(58) Field of Classification Search
CPC ............ A61B 5/04012; A61B 5/04014; A61B 5/04017; A61B 5/048; A61B 5/4064; A61B 5/4082; A61B 5/4836; A61B 5/4839; A61B 5/4848; A61B 5/6868; A61B 5/7282

See application file for complete search history.

(56) References Cited

U.S. PATENT DOCUMENTS

| | | | |
|---|---|---|---|
| 7,324,851 | B1 | 1/2008 | DiLorenzo |
| 8,078,281 | B2 | 12/2011 | Priori et al. |
| 8,190,251 | B2 | 5/2012 | Molnar et al. |
| 2003/0100931 | A1 | 5/2003 | Mullett |
| 2004/0111127 | A1* | 6/2004 | Gliner ................ A61N 1/36082 607/45 |
| 2007/0225674 | A1* | 9/2007 | Molnar .............. A61N 1/36067 604/503 |
| 2009/0018619 | A1 | 1/2009 | Skelton et al. |
| 2009/0082691 | A1 | 3/2009 | Denison et al. |
| 2010/0010392 | A1 | 1/2010 | Skelton et al. |
| 2010/0100153 | A1 | 4/2010 | Carlson et al. |
| 2010/0228314 | A1 | 9/2010 | Goetz |
| 2011/0196446 | A1 | 8/2011 | Wu et al. |
| 2011/0270348 | A1 | 11/2011 | Goetz |
| 2011/0313483 | A1 | 12/2011 | Hincapie Ordonez et al. |
| 2012/0027375 | A1 | 2/2012 | Yasui |
| 2012/0150256 | A1 | 6/2012 | Martens |
| 2012/0271189 | A1* | 10/2012 | Nelson ................. A61B 5/0476 600/544 |
| 2012/0271375 | A1* | 10/2012 | Wu .................... A61N 1/36171 607/45 |
| 2013/0053722 | A1 | 2/2013 | Carlson et al. |
| 2013/0197605 | A1 | 8/2013 | Carlson et al. |
| 2013/0218232 | A1 | 8/2013 | Giftakis et al. |
| 2014/0163627 | A1* | 6/2014 | Starr .................. A61N 1/36067 607/3 |
| 2014/0213926 | A1 | 7/2014 | Vaidyanathan |
| 2014/0221848 | A1 | 8/2014 | Nagasaka |
| 2014/0277235 | A1 | 9/2014 | An et al. |
| 2014/0350634 | A1 | 11/2014 | Grill et al. |
| 2014/0358024 | A1 | 12/2014 | Nelson et al. |
| 2015/0202447 | A1 | 7/2015 | Afshar et al. |
| 2015/0246233 | A1 | 9/2015 | Kaemmerer |
| 2016/0184589 | A1* | 6/2016 | Li ...................... A61N 1/36067 607/45 |
| 2018/0085572 | A1 | 3/2018 | Stanslaski et al. |
| 2018/0085585 | A1 | 3/2018 | Stanslaski et al. |
| 2018/0085586 | A1 | 3/2018 | Stanslaski et al. |

OTHER PUBLICATIONS

Beudel, et al., "Adaptive deep brain stimulation in Parkinson's disease," Parkinsonism and Related Disorders 22, Jan. 2016, S123-S126.

Examination Report from counterpart European Application No. 15702086.8, dated Feb. 12, 2018, 5 pp.

Goetz, et al., "Movement Disorder Society-Sponsored Revision of the Unified Parkinson's Disease Ratings Scale (MDS-UPDRS): Scale Presentation and Clinimetric Testing Results," Movement Disorders, vol. 23, No. 15, Nov. 2008, pp. 2129-2170.

Hickey, et al., "Deep Brain Stimulation: A Paradigm Shifting Approach to Treat Parkinson's Disease," Frontiers in Neuroscience, Apr. 2016, vol. 10, Article 173, 11 pp.

International Preliminary Report on Patentability and Written Opinion from International Application No. PCT/US2015/011829, dated Jul. 28, 2016, 10 pp.

International Search Report and Written Opinion from counterpart International Application No. PCT/US2015/011829, dated Mar. 26, 2015, 14 pages.

Little, et al., "Adaptive Deep Brain Stimulation in Advanced Parkinson Disease," Ann Neurol 2013; Sep. 2013; 74: 449-457.

Little, et al., "Bilateral adaptive deep brain stimulation is effective in Parkinson's disease," J. Neurol Neurosurg Psychiatry; Oct. 26, 2015; 6 p.

Little, et al., "Controlling Parkinson's Disease with Adaptive Deep Brain Stimulation," J. Visualized Experiments, Jul. 16, 2014, 5 pp.

Little, et al., "What brain signals are suitable for feedback control of deep brain stimulation in Parkinson's disease?" Annals of the New York Academy of Sciences, Jul. 25, 2012; pp. 9-24.

U.S. Appl. No. 15/714,888, filed by Stanslaski, et al., filed Sep. 25, 2017.

Prosecution History from U.S. Appl. No. 14/599,126, dated Mar. 29, 2016, through Mar. 22, 2018, 126 pp.

Response to Examination Report from counterpart European Application No. 15702086, dated Feb. 12, 2018, filed Jun. 22, 2018, 8 pp.

Decision to Grant from counterpart European Application No. 15702086, dated Mar. 7, 2019, 2 pp.

\* cited by examiner

MOVEMENT DISORDER SYMPTOM CONTROL

This application is a continuation of U.S. application Ser. No. 14/599,126 filed Jan. 16, 2015, which claims the benefit of U.S. Provisional Application Ser. No. 61/928,859, filed Jan. 17, 2014, the entire contents of each of which is hereby incorporated by reference.

TECHNICAL FIELD

The disclosure relates to controlling a patient's movement disorder symptoms.

BACKGROUND

Nervous system disorders affect millions of people, causing a degradation of life, and in some cases, death. Nervous system disorders may include disorders of the central nervous system and peripheral nervous system. Some nervous system disorders may be considered "neurological movement disorders," and may include, for example without limitation, epilepsy, Parkinson's disease, essential tremor, dystonia, and multiple sclerosis (MS). Neurological movement disorders may be characterized by periods of involuntary movements and/or loss of muscle control.

As an example of a neurological movement disorder, Parkinson's Disease (PD) is generally characterized by poverty and slowness of movement (akinesia and bradykinesia), muscle stiffness (rigidity), tremor at rest, and gait and balance abnormalities that may lead to an inability to perform normal daily life activities. Some patients suffering from neurological movement disorders may also develop symptoms called dyskinesias and motor fluctuations, which may be side effects of certain anti-Parkinson's medication. It is believed that PD is caused by the degeneration of dopaminergic neurons in the substantia nigra pars compacta, a brain structure of the basal ganglia involved in the control of movement. The loss of dopamine in the basal ganglia is believed to secondarily cause a cascade of abnormal activity in the other nuclei of the basal ganglia, thalamus and cortex. This has been detected in animals and humans as changes in neuronal firing patterns, firing frequencies, and in the tendency of these neurons to fire in an oscillatory manner. These abnormal oscillations and firing patterns are thought to underlie the classic motor symptoms of PD and have been shown to be reversible with the dopamine medication used to effectively treat PD.

There are various approaches in treating nervous system disorders, such as neurological movement disorders. Treatment therapies can include any number of possible modalities alone or in combination including, for example, electrical stimulation, magnetic stimulation, drug infusion, and/or brain temperature control. Each of these treatment modalities may be employed using closed-loop feedback control. Such closed-loop feedback control techniques may control stimulation based on received neurological signals (e.g., from a monitoring element) carrying information about a symptom or a condition of a nervous system disorder. Such a neurological signal can include, for example, electrical signals (such as local field potentials (LFPs), electroencephalogram (EEG), electrocorticogram (ECoG), and/or electrocardiogram (EKG) signals), chemical signals, and/or other types of biological signals (such as changes in the quantity of neurotransmitters).

For example, U.S. Pat. No. 8,190,251 to Molnar et al, issued May 29, 2012, incorporated herein by reference in its entirety, discloses determining biomarkers for patients with movement disorders and providing a closed-loop feedback signal to control delivery of therapy.

SUMMARY

In general, the disclosure is directed to detecting one or more biomarkers indicative a patient's current symptoms of a neurological movement disorder. In particular, a signal indicative of brain activity from one or more of a patient's motor cortex and subthalamic nucleus is monitored. Based on the presence or absence of certain predetermined features within the monitored signal, a therapy program may be selected to treat the patient's current symptoms.

In one example, the disclosure is directed to a method which comprises acquiring, with a medical device, at least one electrical signal from a brain of a patient; determining whether at least a first predetermined biomarker and/or a second predetermined biomarker are present in the at least one electrical signal; and determining, based on whether or not the first predetermined biomarker is present and whether or not the second predetermined biomarker is present, a patient state.

In one example, the disclosure is directed to a method which comprises acquiring, with a medical device, at least one electrical signal from a brain of a patient; determining whether at least a first predetermined biomarker and/or a second predetermined biomarker are present in the at least one electrical signal; and adjusting at least one therapy parameter based on whether or not the first predetermined biomarker is present and whether or not the second predetermined biomarker is present.

In one example, the disclosure is directed to a system comprising: an implantable medical device comprising a processor; and a first electrode in communication with the implantable medical device, the first electrode configured to acquire at least one electrical signal from a brain of a patient; and wherein the processor is configured to: determine whether at least a first predetermined biomarker and/or a second predetermined biomarker are present in the at least one electrical signal; and determine based on whether or not the first predetermined biomarker is present and whether or not the second predetermined biomarker is present, a patient state.

In one example, the disclosure is directed to a system comprising: an implantable medical device comprising a processor; and a first electrode in communication with the implantable medical device, the first electrode configured to acquire at least one electrical signal from a brain of a patient; and wherein the processor is configured to: determine whether at least a first predetermined biomarker and/or a second predetermined biomarker are present in the at least one electrical signal; and adjust at least one therapy parameter based on whether or not the first predetermined biomarker is present and whether or not the second predetermined biomarker is present.

In one example, the disclosure is directed to a method which comprises acquiring, with a medical device, a first electrical signal from a motor cortex of a brain of a patient; acquiring, with the medical device, a second physiological signal from a subthalamic nucleus (STN) of a brain of a patient; determining whether at least a first predetermined biomarker is present in the first electrical signal; determining whether at least a second predetermined biomarker is present in the second electrical signal; and adjusting at least one therapy parameter based on whether or not the first predetermined biomarker is present and whether or not the second predetermined biomarker is present.

In another example, the disclosure is directed to an implantable medical device comprising a memory and a processor; a first electrode in communication with the implantable medical device, the first electrode configured to acquire a first electrical signal from a motor cortex of a brain of a patient; and a second electrode in communication with the implantable medical device, the second electrode configured to a second physiological signal from a subthalamic nucleus (STN) of a brain of a patient; and wherein the processor is configured to: determine whether at least a first predetermined biomarker is present in the first electrical signal; determine whether at least a second predetermined biomarker is present in the second electrical signal; and adjust at least one therapy parameter based on whether or not the first predetermined biomarker is present and whether or not the second predetermined biomarker is present.

In one example, the disclosure is directed to a method comprising acquiring, with a medical device, at least one electrical signal from a brain of a patient; determining whether at least a first predetermined biomarker is present in the at least one electrical signal; determining whether at least a second predetermined biomarker is present in at least one electrical signal; and based on whether or not the first predetermined biomarker is present and whether or not the second predetermined biomarker is present, either adjusting at least one therapy parameter, or determining a patient state.

In another example, the disclosure is directed to a system comprising A system comprising: an implantable medical device comprising a memory and a processor; at least a first electrode in communication with the implantable medical device, the first electrode configured to acquire at least one electrical signal from a brain of a patient; wherein the processor is configured to: determine whether at least a first predetermined biomarker is present in the at least one electrical signal; whether at least a second predetermined biomarker is present in the at least one electrical signal; and based on whether or not the first predetermined biomarker is present and whether or not the second predetermined biomarker is present, either adjust at least one therapy parameter, or determine a patient state.

In one example, the disclosure is directed to a system comprising means for acquiring, with a medical device, at least one electrical signal from a brain of a patient; means for determining whether at least a first predetermined biomarker is present in the at least one electrical signal; means for determining whether at least a second predetermined biomarker is present in at least one electrical signal; and either means for adjusting at least one therapy parameter based on whether or not the first predetermined biomarker is present and whether or not the second predetermined biomarker is present, or means for determining a patient state based on whether or not the first predetermined biomarker is present and whether or not the second predetermined biomarker is present.

The details of one or more examples of the present disclosure are set forth in the accompanying drawings and the description below. Other features, objects, and advantages of the techniques discussed in this disclosure will be apparent from the description and drawings, and from the claims.

DETAILED DESCRIPTION

Figure 1:
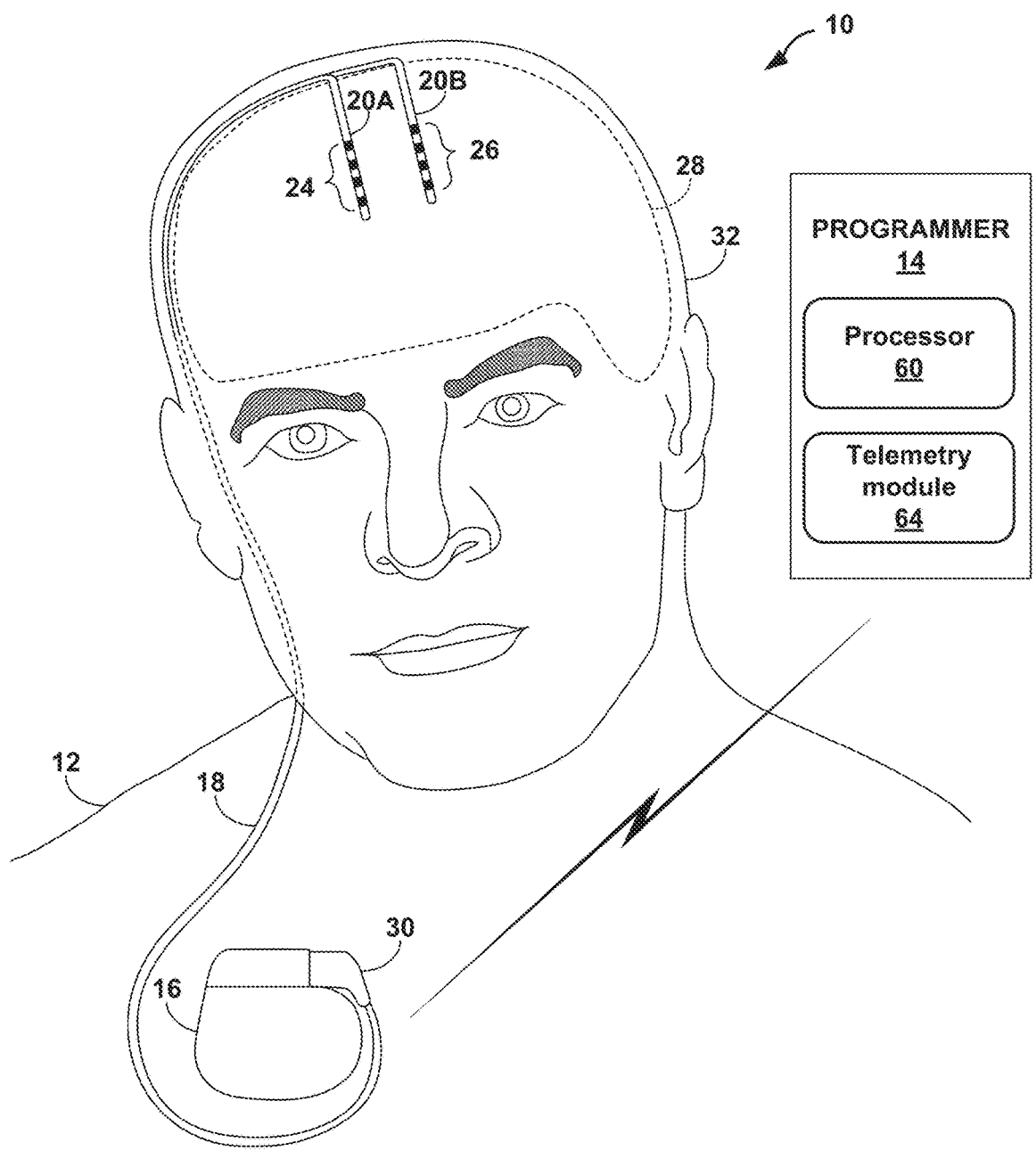
FIG. 1 is a conceptual diagram illustrating an example deep brain stimulation (DBS) system that may be used to implement the techniques of this disclosure.

This disclosure is directed towards a system and method for controlling movement disorder symptoms. In one particular example, the disclosure is directed towards controlling Parkinson's Disease (PD) through automatic titration of treatment. In some examples, the treatment may include a combination of electrical stimulation and medication. In some examples, the treatment may include only electrical stimulation or only medication.

The systems and methods of this disclosure use sensed brain activity to determine whether one or more disease state biomarkers are present. Brain activity may be recorded, for example, in the form of local field potential (LFP) and/or electroencephalogram (EEG) or electrocorticogram (ECoG) signals sensed by an implantable or external medical device. Entrainment generally refers to the process of using stimuli to affect brain activity, e.g., oscillations within a frequency band in the brain. Gamma frequency band oscillations, e.g., ordinarily between about 35 Hertz (Hz) and about 120 Hz or more, in the central nervous system (CNS), recorded using LFP and EEG, for example, are associated with normal information processing in movement and sensory structures. Beta frequency band oscillations between about 8 Hz and about 35 Hz, have been associated with dysfunctions of CNS circuits that control behavioral movements and cognitive states. Higher frequency stimulation, e.g., about 130 Hz, of subcortical brain areas involved with movement, e.g., subthalamic nucleus, globus pallidus internus, and ventralis intermedius nucleus of the thalamus, may reduce behaviors associated with essential tremor and Parkinson's disease such as rigidity, bradykinesia and tremor.

In general, PD patients have phasic changes in their levels of symptom relief and side effects as medication is absorbed into the blood stream, and then is eliminated. For example, a PD patient may show signs of dystonia when not on medication or receiving stimulation. As the treatment (either medication or stimulation) reaches the therapeutic window, the dystonia symptoms subside. In some cases, the medication or stimulation may "overshoot" the therapeutic window, resulting in side effects, such as dyskinesia. As the medication/stimulation wears off, the patient may again enter the therapeutic window where PD symptoms such as dystonia are under control without substituting dyskinesia for the dystonia present when untreated. As the medication continues to be eliminated from the patient, the dystonia may reappear. The intent of the system and method of this disclosure is to adjust a patient's treatment in order to maintain the patient within a therapeutic window where symptoms of PD are under control and side effects from therapy are minimized. In some examples consistent with the present disclosure, stimulation may be used to even out, i.e., smoothly distribute, the therapeutic effect of the natural drug cycle. For example, while the medication is being absorbed, and prior to reaching a concentration within the therapeutic window, electrical stimulation may be used to enhance the therapeutic effects of the medication. As the drug concentration increases, the stimulation may be lessened. If the drug concentration exceeds the therapeutic concentration, resulting in side effects, electrical stimulation may be used to dampen the effect of the drug or combat the side effects caused by the excessive drug concentration. In other examples, movement disorder symptoms may be controlled in a closed-loop fashion using only electrical stimulation, or only medication.

Figure 8:
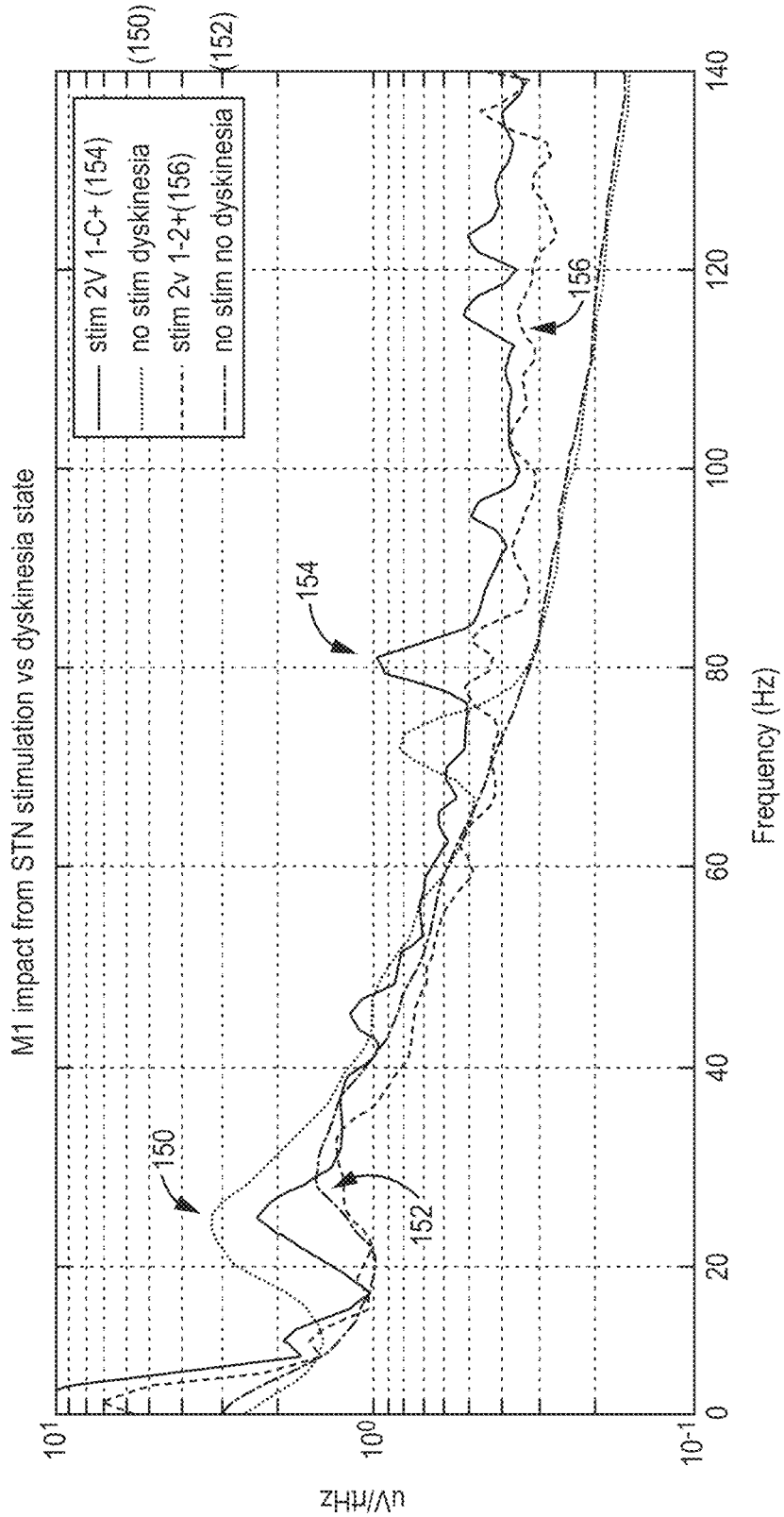
FIG. 8 is a graph showing the impact on the LFP signal of motor cortex from subthalamic nucleus (STN) Stimulation.
Figure 9:
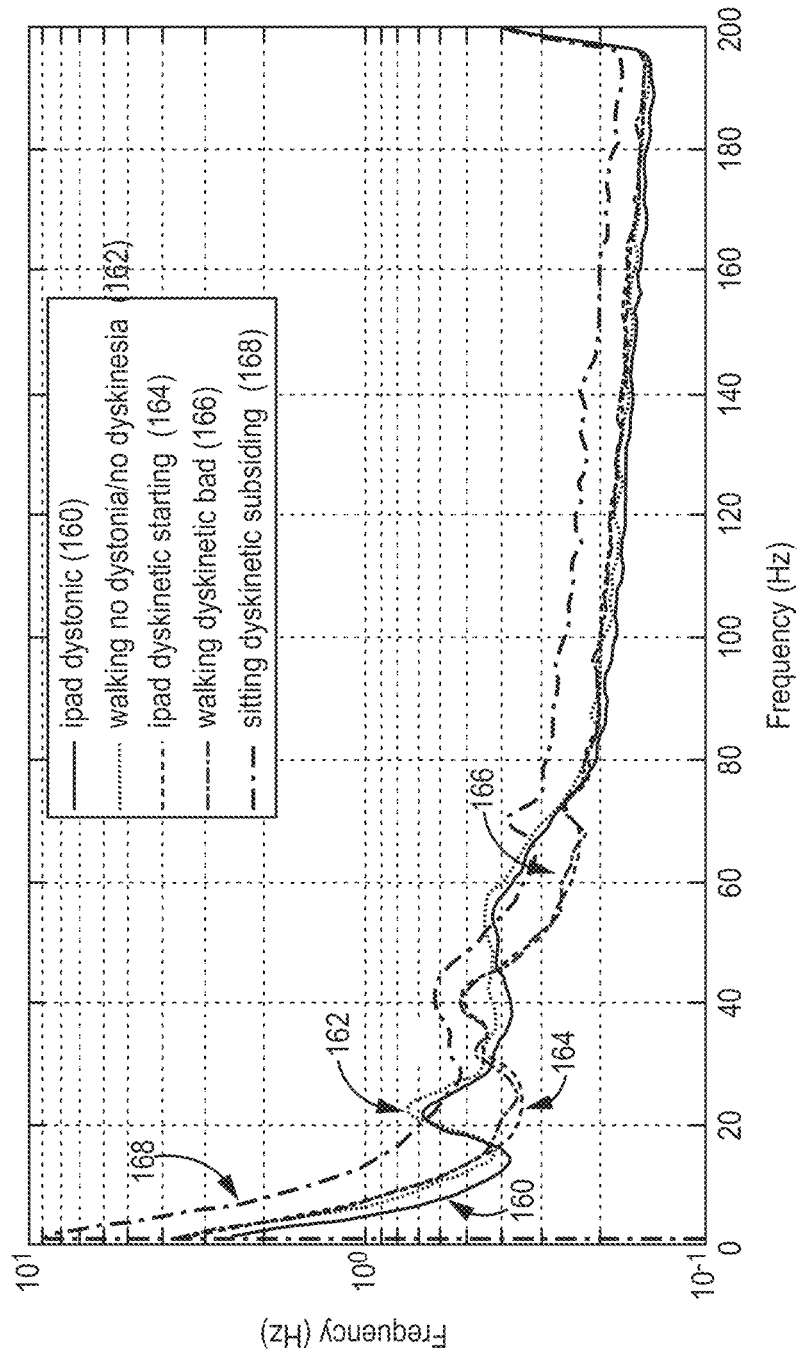
FIG. 9 is a graph showing LFP signals collected from a patient's STN.
Figure 10:
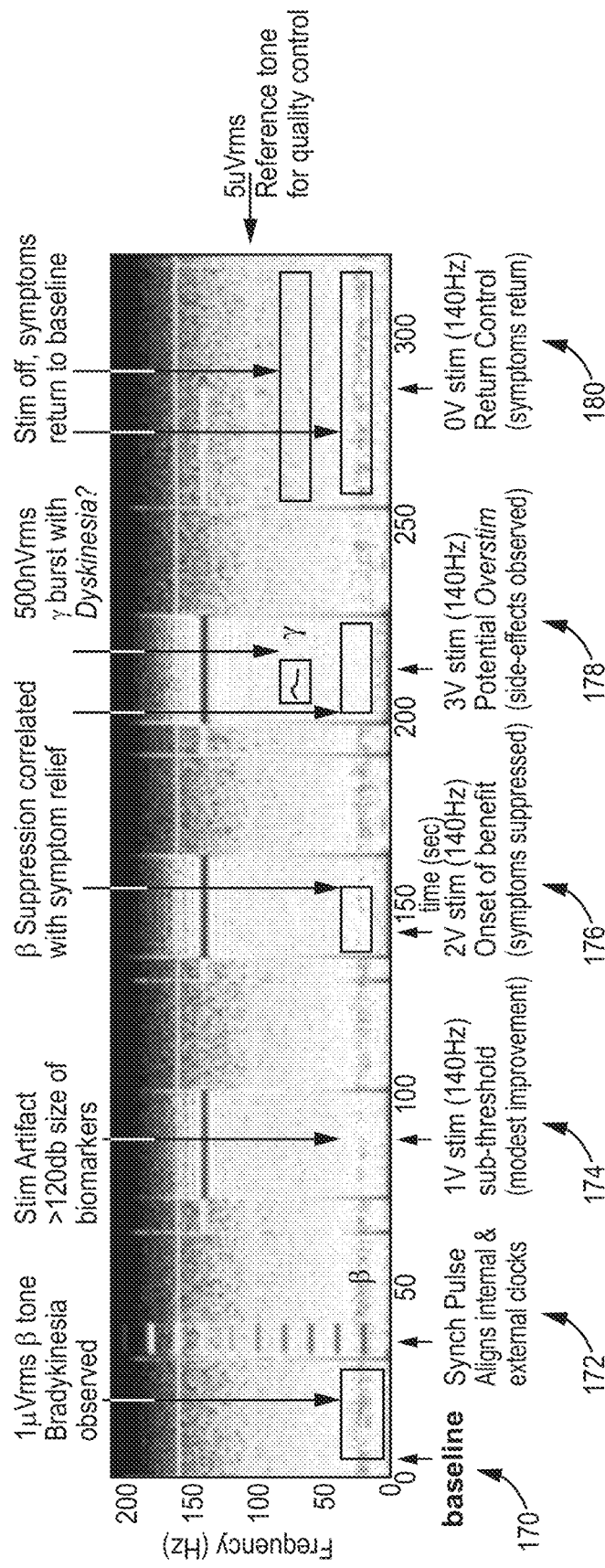
FIG. 10 is a graph showing an LFP signal collected over time while electrical stimulation is provided to a patient.

Brain signals from PD patients include several biomarkers that may be used to indicate when adjustments to patient treatment may be beneficial to keep a patient within the therapeutic window. Brain signals may be collected from, for example, the patient's motor cortex, zona incerta (Zi), subthalmic nucleus (STN), basal ganglia, cerebellum, pedunculopontine nucleus, red nucleus, or lateral globus pallidus. The signals from the motor cortex may be collected from the primary motor cortex (M1), the premotor cortex, the supplementary motor area (SMA), the posterior parietal cortex, or the primary somatosensory cortex. One or more biomarkers may be found in the signals collected from each region of the brain. As shown in FIGS. 8-10 and discussed in more detail below, a PD patient's motor cortex and STN include several biomarkers. For example, a LFP of a PD patient's motor cortex may include a peak in the gamma band when too much medication or stimulation has been provided. The peak in the gamma band may decrease as the side effects from over medication wear off. In addition, a peak may appear in the lower end of the beta range with a high amplitude, when a patient is displaying dyskinesia. As the dyskinesia subsides and the patient returns to the therapeutic window, the frequency of the peak in the beta band increase, and the amplitude decreases.

An LFP of a PD patient's STN may also include specific frequency signatures, or biomarkers. For example, the LFP of a patient prior to receiving medication may include a peak within the beta band that subsides as the concentration of medication increases. As the medication takes effect, the beta peak shifts to a higher frequency range. In addition, when over medication has occurred a small peak shows up within the gamma range. These biomarkers shown in the LFP of a patient's motor cortex and STN may be used to create an algorithm which automatically adjusts electrical stimulation and/or drug delivery in a patient in order to maintain a patient within the therapeutic window.

Thus, a parameter of the measured brain activity, such as a biomarker, may be defined from measured LPF signals from the patient's motor cortex and STN. The biomarkers may be monitored by an implantable medical device (IMD) or external programmer or controller. The biomarkers may be used to assess the patient's current disease state. The biomarker may also be used to serve as an indicator of therapy effectiveness in a device or system. Further, the biomarker may provide feedback to control the IMD. In some examples, information regarding one or more patient specific biomarkers may allow for an enhanced ability to provide individualized therapy.

Certain examples consistent with the present disclosure include an implantable medical device and/or lead system adapted to electrically stimulate targets in the brain to modulate one or more biomarkers indicative of PD. The IMD may continually adjust one or more therapy parameters to maintain certain biomarkers, and suppress others that indicate the patient is within a therapeutic window which provide optimum symptom control with minimal side-effects.

In some examples, a medical device may control the delivery of stimulation based the presence of one or more biomarkers in either the beta or gamma frequency ranges. The electrical simulation may include delivering stimulation at approximately 55-65 Hz in order to reduce tremor or dyskinesia. In some examples, the electrical stimulation may be delivered at approximately 60 Hz. The approximately 55-65 Hz stimulation should modulate the biomarkers of the patient by reducing low motor cortex beta signals and inducing a higher beta signal. In some examples the approximately 55-65 Hz stimulation modulates the biomarkers of the patient by reducing low M1 beta signals and inducing a higher beta signal. The medical device may deliver stimulation at approximately 120-140 Hz, thereby reducing bradykinesia and rigidity. In some examples, the medical device may deliver stimulation at approximately 130 Hz. The stimulation at approximately 120-140 Hz may modulate the biomarkers of the patient to reduce the presence of a STN low beta peak. In some examples, the medical device may provide burst stimulation with short inter-cycle intervals to decrease power at various frequencies. In some examples, burst stimulation may be provided at approximately the same frequency as the biomarker to be modulated. The burst stimulation may comprise cycling between stimulation being provided, and stimulation being off. In some examples, the interval between providing stimulation may be short. In some examples, the medical device may alternate between delivery of stimulation at approximately 60 Hz and stimulation at approximately 130 Hz.

FIG. 1 is a conceptual diagram illustrating an example deep brain stimulation (DBS) system that may be used to implement the techniques of this disclosure. In FIG. 1, example therapy system 10 may deliver electrical stimulation therapy to control a patient condition, such as a movement disorder or a neurodegenerative impairment of patient 12. Patient 12 ordinarily will be a human patient. In some cases, however, therapy system 10 may be applied to other mammalian or non-mammalian non-human patients. While movement disorders and neurodegenerative impairment are primarily referred to in this disclosure, in other examples, therapy system 10 may provide therapy to manage symptoms of other patient conditions, such as, but not limited to, seizure disorders or psychological disorders.

A movement disorder or other neurodegenerative impairment may include symptoms such as, for example, muscle control impairment, motion impairment or other movement problems, such as rigidity, bradykinesia, rhythmic hyperkinesia, non-rhythmic hyperkinesia, and akinesia. In some cases, the movement disorder may be a symptom of PD. However, the movement disorder may be attributable to other patient conditions. Although PD is primarily referred to throughout the remainder of the disclosure, the therapy systems and methods described herein may also useful for controlling symptoms of other conditions, such as other movement disorders or neurodegenerative impairment.

In the example of FIG. 1, therapy system 10 includes medical device programmer 14, implantable medical device (IMD) 16, lead extension 18, and leads 20A and 20B with respective sets of electrodes 24, 26. In some examples (not shown), therapy system 10 may include one or more additional medical devices, which may also be in communication with medical device programmer 14. In the example shown in FIG. 1, electrodes 24, 26 of leads 20A, 20B are positioned to sense LFPs and/or deliver electrical stimulation to a tissue site within brain 28, such as a deep brain site under the dura mater of brain 28 of patient 12. In some examples, delivery of stimulation to one or more regions of brain 28, such as the subthalamic nucleus (STN), globus pallidus internus (GPi), motor cortex such as M1, or thalamus, may be an effective treatment to manage movement disorders, such as Parkinson's Disease or essential tremor.

IMD 16 includes a therapy module that includes a stimulation generator that generates and delivers electrical stimulation therapy to patient 12 via a subset of electrodes 24, 26 of leads 20A and 20B, respectively. The subset of electrodes 24, 26 that are used to deliver electrical stimulation to patient 12, and, in some cases, the polarity of the subset of electrodes 24, 26, may be referred to as a stimulation electrode combination.

Using the techniques described in this disclosure, a subset of electrodes 24, 26 of leads 20A and 20B, respectively, may be used to deliver electrical stimulation to patient 12 in order to re-establish, or re-induce, gamma frequency band activity within brain 28. As mentioned above, gamma frequency band activity may be facilitative of movement and cognitive states, while beta frequency band activity may be inhibitive of movement and perhaps cognitive states. As such, it may be desirable to decrease beta frequency band activity in the brain and increase gamma frequency band activity in the brain.

In some examples, beta frequency band activity in the brain may be decreased and gamma frequency band activity in the brain may be increased by delivering electrical stimulation to a portion of the brain at a frequency some predetermined ratio between the detected activity in the gamma band and the frequency of stimulation. In one example, the frequency of the electrical stimulation delivered to the portion of the brain may be at a constant frequency at some predetermined ratio between the detected activity in the gamma band and the frequency of electrical stimulation. For example, electrodes 24, 26 of leads 20A and 20B, respectively, may be used to deliver electrical stimulation to patient 12 at a frequency shown to affect the individual patient's biomarkers. In some examples, electrical stimulation is provided in a biphasic manner. For example, stimulation may be provided at a particular frequency at a voltage that alternates between +2V and −2V.

In another example, the frequency of the electrical stimulation delivered to the portion of the brain may be applied in a sweeping manner. For example, the frequency of the electrical stimulation may be swept through a range of frequency values. In a frequency sweep, the frequency of the electrical stimulation may begin at one value and then may be varied, e.g., increased or decreased, from a first frequency to a second frequency. For example, electrodes 24, 26 of leads 20A and 20B, respectively, may be used to deliver electrical stimulation to patient 12 in a frequency sweeping manner while the effect of the electrical stimulation on a patient's predetermined biomarkers may be examined. In some examples, a frequency sweep may be performed multiple times, where the patient is in a different state during each sweep. For example, a sweep may be performed while the patient is showing signs of dystonia, another while the patient is within the therapeutic window, and a third while the patient is displaying signs of dyskinesia. In some examples, other electrical stimulation parameters may be adjusted in sweeping manner. For example, stimulation amplitude, or burst frequency may also be tested. As one example, electrodes 24, 26 of leads 20A and 20B may begin delivering electrical stimulation to patient 12 being at a low frequency, which is then swept upwards. For example, electrical stimulation may be delivered in a sweeping manner from beta band frequency to a gamma band frequency (e.g., from about 30 Hz to about 140 Hz) while simultaneously monitoring LFP or EEG activity.

It should be noted that leads 20A, 20B may be separate leads, or bifurcated segments on a single lead. Some example configurations may comprise only a single lead. Two leads support bilateral stimulation in both brain hemispheres while one lead supports unilateral stimulation in one hemisphere. In some examples, one lead is positioned in or near M1 and the other lead is positioned in or near STN. In a frequency sweep, stimulation may be applied at different frequencies in a range of frequencies in a sequence, e.g., by increasing or decreasing by N Hz, where N is any number, in a linear or non-linear manner.

Figure 2:
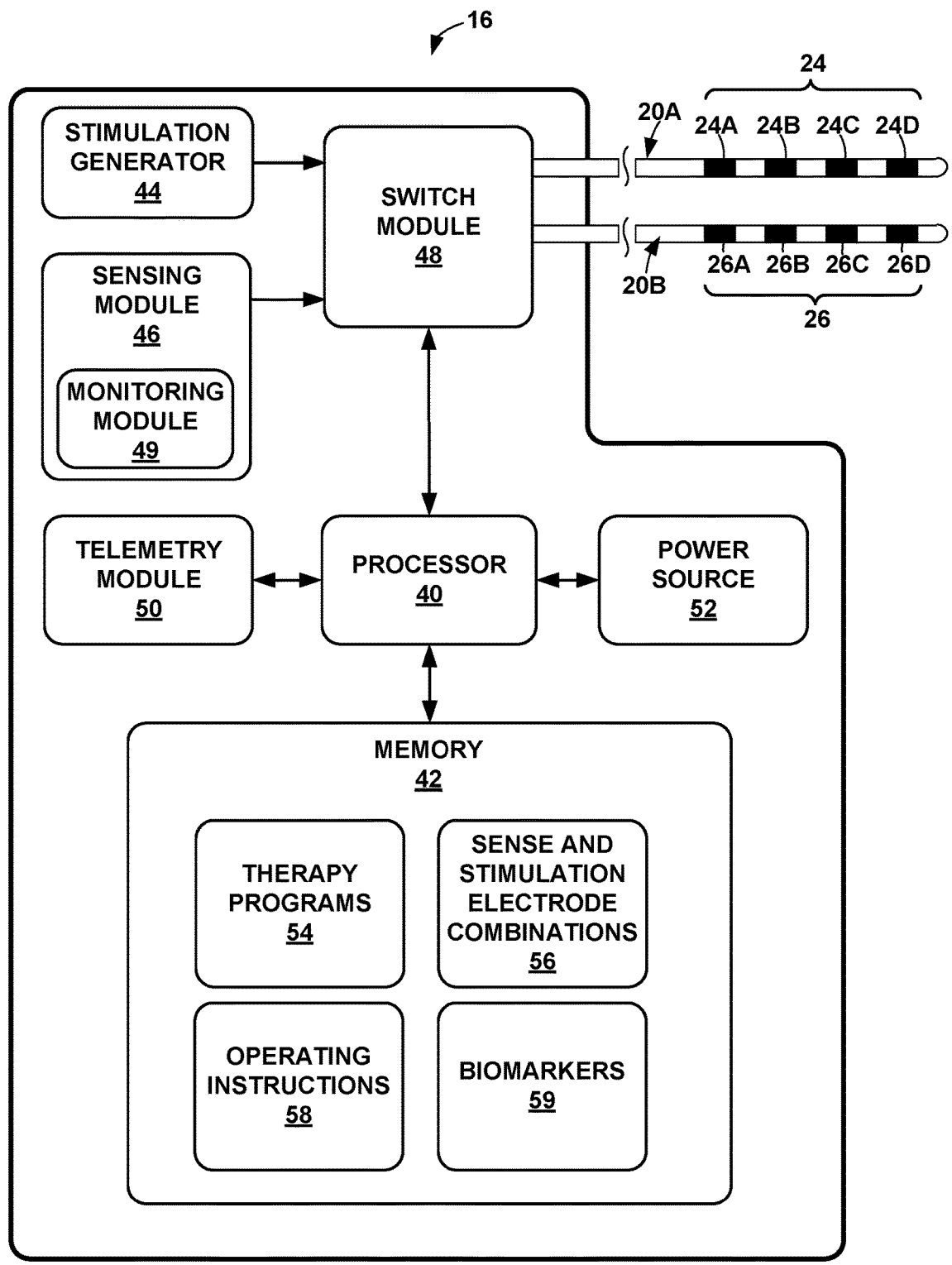
FIG. 2 is functional block diagram illustrating components of an example medical device that may be used to implement the techniques of this disclosure.

FIG. 2 is functional block diagram illustrating components of an example medical device that may be used to implement the techniques of this disclosure. FIG. 2 is a functional block diagram illustrating components of an example IMD 16. In the example shown in FIG. 2, IMD 16 includes processor 40, memory 42, stimulation generator 44, sensing module 46, switch module 48, telemetry module 50, and power source 52. Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 40, cause IMD 16 to perform various functions.

In the example shown in FIG. 2, memory 42 stores therapy programs 54, sense electrode combinations and associated stimulation electrode combinations 56, and operating instructions 58 in separate memories within memory 42. Each stored therapy program 54 defines a particular program of therapy in terms of respective values for electrical stimulation parameters, such as a stimulation electrode combination, electrode polarity, current or voltage amplitude, pulse width, and pulse rate. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis. In some examples, a therapy group may include a set of therapy programs wherein each of the therapy programs is associated with a different combination of biomarkers being present in a physiological signal received from the patient's brain. In some examples, a therapy group may include a combination of stimulation parameters and drug delivery parameters. The therapy groups may be store in memory 42, or another memory within IMD 16 or programmer 14. Memory 42 may also temporarily store the most recently determined biomarkers, and the therapy program currently being applied to the patient.

Sense and stimulation electrode combinations 56 stores sense electrode combinations and associated stimulation electrode combinations. As described above, in some examples, the sense and stimulation electrode combinations may include the same subset of electrodes 24, 26, or may include different subsets of electrodes. Operating instructions 58 guide general operation of IMD 16 under control of processor 40, and may include instructions for measuring the impedance of electrodes 24, 26. Processor 40 may compare received bioelectrical brain signals to values stored as biomarkers 59, as will be discussed in more detail below.

Stimulation generator 44, under the control of processor 40, generates stimulation signals for delivery to patient 12 via selected combinations of electrodes 24, 26. An example range of electrical stimulation parameters believed to be effective in DBS to manage a movement disorder of patient include the following:

1. Frequency: between approximately 20 Hz and approximately 500 Hz, such as between approximately 50 Hz and approximately 150 Hz, or approximately 130 Hz.

2. Voltage Amplitude: between approximately 0.1 volts and approximately 20 volts, such as between approximately 0.5 volts and approximately 10 volts, or approximately 5 volts.

3. Current Amplitude: a current amplitude may be defined as the biological load in which the voltage is delivered. In a current-controlled system, the current amplitude, assuming a lower level impedance of approximately 500 ohms, may be between approximately 0.2 milliamps to approximately 100 milliamps, such as between approximately 1 milliamps and approximately 40 milliamps, or approximately 10 milliamps. However, in some examples, the impedance may range between about 200 ohms and about 2 kilohms.

4. Pulse Width: between approximately 10 microseconds and approximately 5000 microseconds, such as between approximately 100 microseconds and approximately 1000 microseconds, or between approximately 180 microseconds and approximately 450 microseconds.

Stimulation generator 44 may, for example, generate either constant current-based or constant voltage-based stimulation in the form of pulses or continuous waveforms. In delivering constant current-based stimulation, stimulation generator 44 maintains the amplitude of the current at a constant level. In delivering constant voltage-based stimulation, stimulation generator 44 maintains the amplitude of the voltage at a constant level. In other examples, stimulation generator 44 may generate bipolar stimulation.

Accordingly, in some examples, stimulation generator 44 generates electrical stimulation signals in accordance with the electrical stimulation parameters noted above. Other ranges of therapy parameter values may also be useful, and may depend on the target stimulation site within patient 12, which may be within brain 28 or other portions of the nervous system. While stimulation pulses are described, stimulation signals may be of any form, such as continuous-time signals (e.g., sine waves) or the like.

Processor 40 may include any one or more of a microprocessor, a controller, a digital signal processor (DSP), an application specific integrated circuit (ASIC), a field-programmable gate array (FPGA), discrete logic circuitry, and the functions attributed to processor 40 in this disclosure may be embodied as firmware, hardware, software or any combination thereof. In some examples, the DSP may use a fast Fourier transform (FFT) algorithm. Processor 40 controls stimulation generator 44 according to therapy programs 54 stored in memory 42 to deliver, or apply, particular stimulation parameter values specified by one or more of programs, such as amplitude, pulse width, and pulse rate.

In the example shown in FIG. 2, the set of electrodes 24 includes electrodes 24A, 24B, 24C, and 24D, and the set of electrodes 26 includes electrodes 26A, 26B, 26C, and 26D. Processor 40 also controls switch module 48 to apply the stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48.

Stimulation generator 44 may be a single channel or multi-channel stimulation generator. In particular, stimulation generator 44 may be capable of delivering a single stimulation pulse, multiple stimulation pulses or continuous signal at a given time via a single electrode combination, or multiple stimulation pulses or continuous signals at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

Sensing module 46, under the control of processor 40, may sense bioelectrical brain signals and provide the sensed bioelectrical brain signals to processor 40. Processor 40 may control switch module 48 to couple sensing module 46 to selected combinations of electrodes 24, 26, i.e., a sense electrode combination. In this way, IMD 16 is configured such that sensing module 46 may sense bioelectrical brain signals with a plurality of different sense electrode combinations. Switch module 48 may be electrically coupled to the selected electrodes 24, 26 via the conductors within the respective leads 20, which, in turn, deliver the bioelectrical brain signals sensed across the selected electrodes 24, 26 to sensing module 46. The bioelectrical brain signals may include biomarkers, e.g., amplitude and phase relationships, which are indicative of electrical activity within brain 28 of patient 12 and, in particular, electrical activity within one or more frequency bands, e.g., gamma frequency band, beta frequency band, and other frequency bands, of brain 28.

Although sensing module 46 is incorporated into a common housing with stimulation generator 44 and processor 40 in FIG. 2, in other examples, sensing module 46 may be in a separate housing from IMD 16 and may communicate with processor 40 via wired or wireless communication techniques. Example bioelectrical brain signals include, but are not limited to, a signal generated from local field potentials within one or more regions of brain 28. EEG and ECoG signals are examples of local field potentials (LFPs) that may be measured from brain 28. However, local field potentials may include a broader genus of electrical signals within brain 28 of patient 12.

Processor 40 may analyze bioelectrical brain signals in order to determine, for example, whether one or more biomarkers is present within one or more of the beta frequency band, and the gamma frequency band of the patient's motor cortex or STN. For example, sensing module 46 may sense via a subset of electrodes 24,26 (or a different subset of electrodes) bioelectrical brain signals of brain 28, measure an amplitude of the sensed bioelectrical brain signals, and provide the sensed bioelectrical brain signals and measured amplitude to processor 40. Upon receiving the sensed bioelectrical brain signals and measured amplitude, processor 40 may analyze the received signals to determine whether a peak is present in either the motor cortex signal or the STN signal at approximately 20-25 HZ, approximately 25-35 Hz, and/or at approximately 70-75 Hz. Such a peak may be an example biomarker. In some examples, the detected peaks may be compared to predetermined biomarkers 59. In some examples, the amplitude of any peaks presents is also determined. In some examples, the exact location that processor 40 looks for peaks is determined on a patient specific basis. The exact locations may be stored in biomarkers 59.

In accordance with the techniques of this disclosure, processor 40 may select a therapy program from a plurality of therapy programs stored in memory 42, based on the presence of one or more biomarkers in the bioelectrical signals sensed by electrodes 24,26. For example, processor may select a first program if a biomarker from the motor cortex shows a spike in a low beta range (between approximately 20-25 Hz) and a second program if a biomarker from the STN shows a spike in the low beta range. A spike may refer to a peak with an amplitude above a predetermined threshold, or where the ratio of the amplitude to the base of the peak is above a predetermined ratio. In some examples, the first and second programs may be patient specific. For example, the first program may include delivery of stimulation at a particular frequency determined during initial programming of the IMD 16. Similarly, the second program may include delivery of stimulation at a second particular frequency determined during initial programming of the IMD 16.

Sensing module 46 may include frequency monitoring module 49 capable of monitoring bioelectrical brain signals associated with patient 12 in selected frequency bands. Frequency monitoring module 49 may include tunable filtering and amplification capabilities that filter the bioelectrical brain signals into one or more of the beta frequency band, the gamma frequency band, and the theta frequency band, for example, and amplify the resulting filtered signal for analysis by processor 40. That is, frequency monitoring module 49 may be tuned, either by a clinician, patient, or without user intervention (i.e., automatically), to detect bioelectrical brain signals in one or more frequency bands such as the beta frequency band, or the gamma frequency band. Example circuitry capable of filtering and amplifying bioelectrical brain signals is described in U.S. Publication No. 2009/0082691 to Denison et al., entitled, "FREQUENCY SELECTIVE MONITORING OF PHYSIOLOGICAL SIGNALS," which was published on Mar. 26, 2009.

It should be noted that in some example implementations, the bioelectrical brain signals of patient 12 may be analyzed by processor 60 of programmer 14 (or by a computer) and then transmitted via telemetry module 64 to telemetry module 50 of IMD 16.

After stimulation generator 44 delivers the electrical stimulation, or in between electrical stimulation pulses, the sensing module 46 and frequency monitoring module 49 may again monitor bioelectrical brain signals associated with patient 12. Then, processor 40 may analyze the signals to determine whether the delivered electrical stimulation resulted in modulation of one or more previously detected biomarkers. Based on the current biomarkers, processor 40 may modify the therapy being provided to patient 12. Modification may include selecting a different therapy program from memory 42, or adjusting one or more stimulation parameters.

The examples described above utilize closed-loop techniques for the delivery of electrical stimulation. That is, the examples describe sensing module 46 and frequency monitoring module 49 monitoring bioelectrical brain signals, processor 40 analyzing the bioelectrical brain signals and controlling delivery of electrical stimulation based on the analysis, sensing module 46 and frequency monitoring module 49 monitoring bioelectrical brain signals after delivery of the electrical stimulation, and processor 40 determining whether stimulation generator 44 should again deliver electrical stimulation.

The techniques described in this disclosure may be performed in a system that has already been implanted in a patient and programmed, or in clinical settings in which a system is being implanted in a patient and programming is being turned on for the first time. In a clinical implant setting, for example, in addition to or instead of monitoring biomarkers, a clinician may monitor the motor performance, e.g. using the clinical Unified Parkinson's Disease Rating Scale (UPDRS), or similar clinical measure, of a patient. The clinician may use the combination of observed motor performance and bioelectrical signals collected to better identify patient specific biomarkers. A clinician may also use the techniques of this disclosure to deliver electrical stimulation to patient 12 and monitor the motor performance of patient 12 in response to receiving the electrical stimulation. By monitoring the motor performance of patient 12 in response to receiving the electrical stimulation, a clinician may determine efficacious electrical stimulation settings that may be programmed into memory 42. For example, a clinician may determine the patient's efficacious electrical stimulation in a variety of patient states. The patient states may include an unmedicated state where the patient is not receiving any therapy and is displaying symptoms of PD such as bradykinesia, rigidity, dystonia, or tremor; an equilibrium state where the patient's response to therapy includes PD symptoms under control without the presence of side effects; and a side effects state, where the patient is experiencing side effects from over medication such as dyskinesia. The determined stimulation settings may be programmed into memory 42 as part of therapy programs 54 for later use.

Telemetry module 50 supports wireless communication between IMD 16 and an external programmer 14 or another computing device under the control of processor 40. In some examples, telemetry module 50 may support communication between IMD 16 and another medical device (not shown). Processor 40 of IMD 16 may receive, as updates to programs, values for various stimulation parameters such as amplitude and electrode combination, from programmer 14 via telemetry module 50. The updates to the therapy programs may be stored within therapy programs 54 portion of memory 42. Telemetry module 50 in IMD 16, as well as telemetry modules in other devices and systems described herein, such as programmer 14, may accomplish communication by radiofrequency (RF) communication techniques. In addition, telemetry module 50 may communicate with external medical device programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
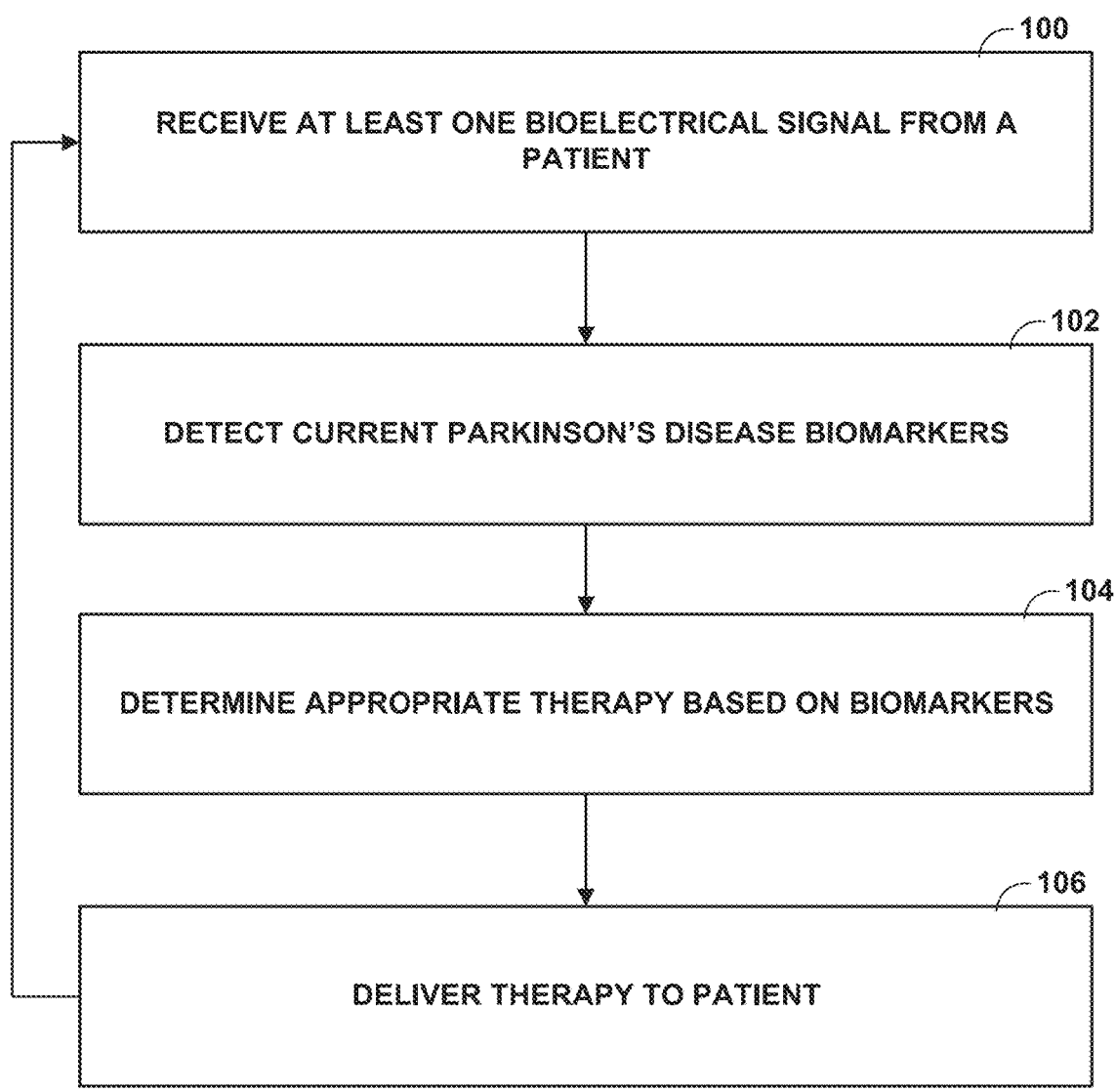
FIG. 3 is a flow chart illustrating an example method of control PD symptoms in a patient.

FIG. 3 is a flow chart illustrating an example method of controlling PD symptoms in a patient. Although described as being carried out within IMD 16, one or more of the steps may be completed by programmer 14. IMD 16 receives, via electrodes 24, 26, at least one bioelectrical signal from a patient (100). In some examples, electrodes 24, 26 may detect a bioelectrical signal from one or more of the motor cortex, the STN, the Zi, the GPi and the GPe. In some examples, a signal from the motor cortex may be from the M1. In some examples, electrodes 24 and 26 may detect LFPs in both the STN and motor cortex the patient's brain. Monitoring module 49 may monitor one or more frequency bands within the received bioelectrical signals. For example, monitoring module 49 may monitor both the beta and gamma bands of the detected LFPs from the patient's STN and motor cortex. Based on the received bioelectrical signals, processor 40 may detect the patient's current PD biomarkers (102). In some examples, processor 40 may determine whether at least a first and second predetermined biomarker are present in the received bioelectrical signal.

In some examples, processor 40 may determine whether biomarkers are present in both a signal from the patient's STN and from the patient's motor cortex. Processor 40 may determine whether the STN signal includes a beta peak between approximately 20-25 Hz, a beta peak between approximately 25-35 Hz, and/or a gamma peak between approximately 70-75 Hz, as biomarkers. In some examples, processor 40 will further differentiate between a beta peak between 20-25 Hz and one between 25-35 Hz by determining the amplitude and width of the peak. For example, processor 40 may look for a narrow, relatively high amplitude peak between approximately 20 and 25 Hz, but a broader and lower amplitude peak between 25 and 35 Hz. A high amplitude peak between 20 and 25 Hz may indicate the patient is experiencing dystonia, while a broader lower amplitude peak between 25 and 35 Hz may indicate the patient is currently within the therapeutic window. In some examples, processor 40 may also determine one or more biomarkers present in the motor cortex signal. For example, the processor may determine whether the motor cortex signal includes a beta peak between approximately 20-35 Hz, and/or a gamma peak between approximately 70-80 Hz. In some examples, processor 40 will further differentiate between a low beta peak in the range of approximately 20-25 Hz with a high amplitude, and a high beta peak in the range of approximately 25-35 Hz with a broader base and a lower amplitude.

Processor 40 may determine an appropriate therapy based on detected current biomarkers (104). In some examples, the determination of appropriate therapy may be made without user intervention (i.e., automatically). In some examples, processor 40 may first determine a patient state based on the determined biomarkers, and select therapy parameters based on the determined patient state. In some examples, a low beta peak in the motor cortex signal may indicate a patient is experiencing dyskinesia from overmedication. In response, processor 40 may instruct stimulation generator 44 to apply stimulation at approximately 55-65 Hz to the STN in order to artificially raise and broaden the motor cortex signal beta peak to between approximately 25-35 Hz, thus lowering the presence of side effects from over medication. In some examples, a low beta peak in the STN signal may indicate that the patient is experiencing either dystonia or tremors. Processor 40 may instruct stimulation generator 44 to apply stimulation at approximately 60 Hz to the STN in order to artificially raise and broaden the beta peak to between approximately 25-35 Hz, thus reducing the presence of tremors. In some examples, stimulation generator 44 may apply stimulation at approximately 130 Hz in response to low beta peak in the STN signal. In some examples, in response to a peak in the gamma frequency in either the STN signal or the motor cortex signal, processor 40 may instruct stimulation generator 44 to apply burst stimulation in order to decrease the peaks in the gamma frequency. For example, burst stimulation at approximately the same frequency as the detected peaks may be applied to the STN. In some examples, processor 40 may retrieve one or more therapy programs 54 from memory 42 based on the detected biomarkers. In some examples, the processor of programmer 14 may direct a second medical device to adjust the dosage of one or more drugs delivered to the patient. For example, programmer 14 may direct the second medical device to modify the rate of release of a medication, or the frequency of delivery of a bolus of medication. In some examples, the selection of a therapy program 54 may take into consideration when and how much drug has been delivered to the patient previously. Based on the therapy selected from memory 42 or otherwise determined by processor 40, processor 40 directs the delivery of therapy to the patient (106). As discussed above, the therapy may include stimulation at approximately 55-65 Hz, stimulation at approximately 120-140 Hz, burst stimulation, stimulation at the send frequency, delivery of a drug dosage, and/or a modification to the amount of drugs delivered. After the delivery of therapy, IMD 16 continues to monitor at least one bioelectrical signal from the patient. In this way, IMD 16 may determine the effect of the most recent therapy delivery, as well as maintain the patient within a therapeutic window in which the patient's PD symptoms are minimized along with minimal side effects.

Figure 4:
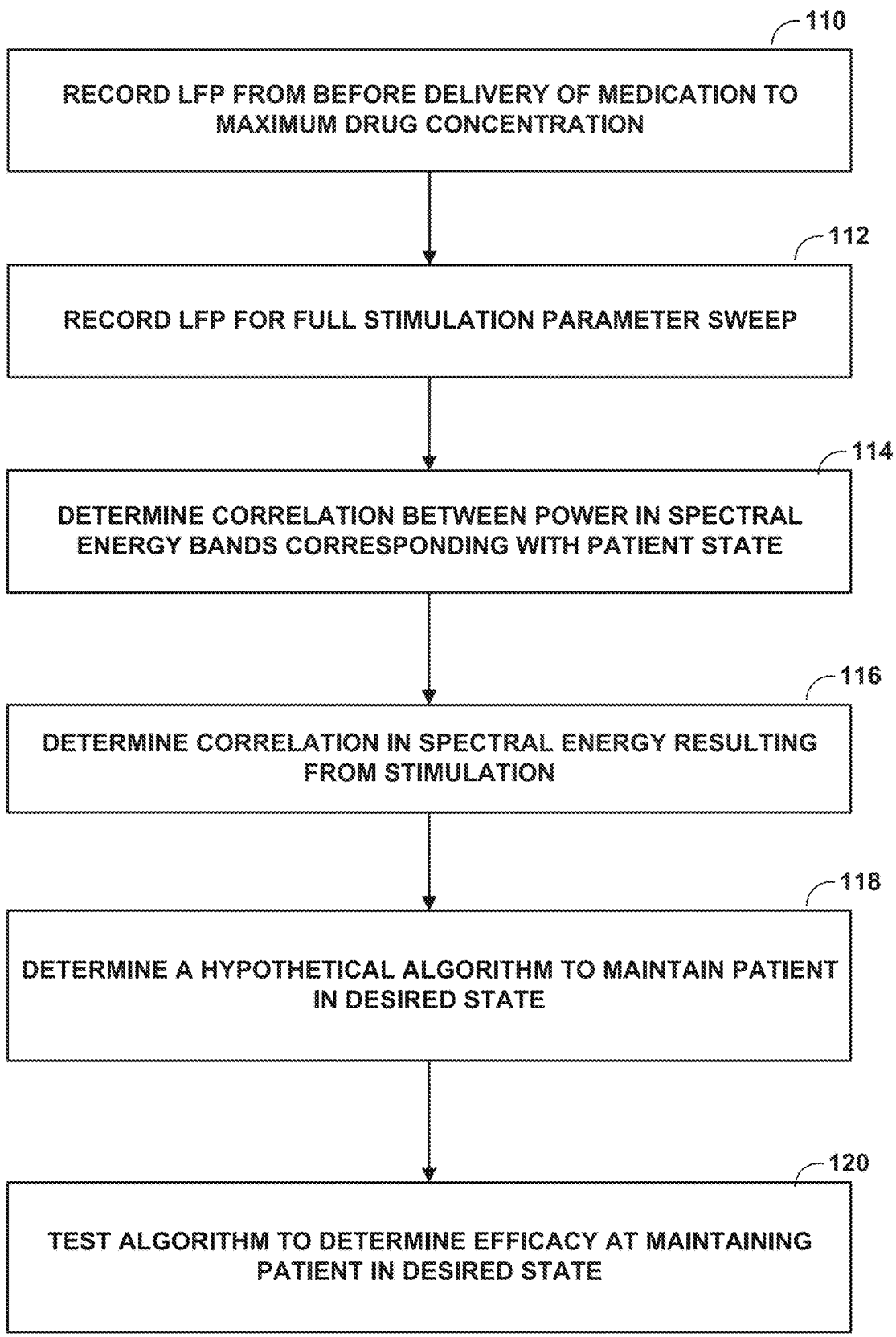
FIG. 4 is a flow chart illustrating an example method of determining patient specific titration control policies.

FIG. 4 is a flow chart illustrating an example method of determining patient specific titration control policies. A patient begins a programming session in a state without medication or therapy being applied. Programmer 14 may record one or more LFPs obtained over a period of time from before delivery of medication to a time at which maximum drug concentration in the patient has been reached (110). After programmer 14 has begun recording the LFPs, a PD patient's normal medication may be delivered. In some examples, the one or more LFPs may be recorded during an entire cycle of drug absorption and dissipation. In some examples, the patient or a clinician may enter information into programmer 14 during the drug cycle, including, for example, the patient's current symptoms. In some examples, the patient indicates when the best achievable medication effect has occurred. In some examples, the LFP for both the motor cortex and the STN are recorded in programmer 14. Programmer 14 may also record LFP for a full stimulation parameter sweep (112). In some examples, the programmer may control IMD 16 to perform a frequency sweep. In some examples, the sweep may start at approximately 30 Hz and increase to approximately 160 Hz. In some examples, programmer 14 may control IMD 16 to sweep through one or more other stimulation parameters such as amplitude or burst rate. The processor of IMD 16 or programmer 14 then determines correlations between power in spectral energy bands corresponding with patient state (114). One or more patient states may include, for example, under-medicated or presence of PD symptoms; overmedicated or presence of side effects; and best achievable effect, or when the patient is within the therapeutic window for a given drug dosage. The correlation between any peaks present in the LFP signal and the patient state at the time the LFP signal is received may be stored in Memory 42. In addition, programmer 14 determines a correlation in spectral energy resulting from the application of stimulation (116). For example, programmer 14 may use a transfer function to help determine the correlation between various peaks in the detected LFPs and the stimulation provided at that time. In other examples, programmer 14 may determine the correlation between various peaks in the detected LFPS, the stimulation provided, and the patient state. Based on the correlations between patient state and power in spectral energy bands, as well as correlations between spectral energy and stimulation parameters, programmer 14 may determine a hypothetical algorithm to maintain a patient in the desired state (118). In some examples, the hypothetical algorithm may be generated by a clinician. Programmer 14 then directs IMD 16 to apply the algorithm, and programmer tests the algorithm to determine efficacy at maintaining the patient in the desired state (120). Testing the algorithm includes observing one or more of the patient's LFPs during application of the algorithm to titrate patient treatment. In some examples, based on how well the hypothetical algorithm works, adjustments may be made to the hypothetical algorithm.

Figure 5:
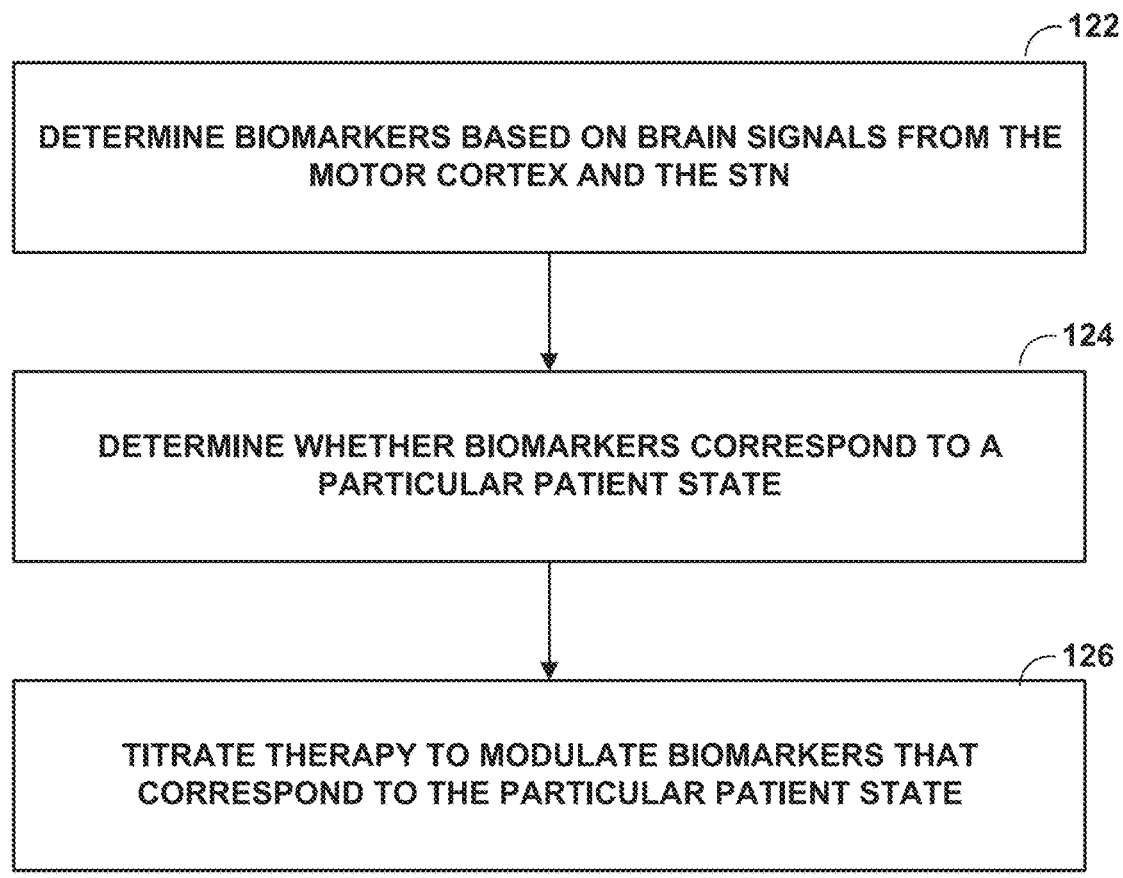
FIG. 5 is a flow chart illustrating an example method of determining adjustments to a patient's PD treatment.

FIG. 5 is a flow chart illustrating an example method of determining adjustments to a patient's PD treatment. Processor 40 of IMD 16 determines biomarkers based on brain signals from the motor cortex and the STN (122). In some examples, the motor cortex signal is from the M1. In some examples, the brain signals received by IMD 16 are LFPs. In some examples, the biomarkers include one or more of a low beta peak in the STN signal, a low beta peak in the motor cortex signal, a high beta peak in the STN signal, a high beta peak in the motor cortex signal, a gamma peak in the STN signal, and a gamma peak in the motor cortex signal. A low beta peak in either the motor cortex signal or the STN signal may be between approximately 20 and 25 Hz. A high beta peak in either the motor cortex signal or the STN signal may be between approximately 25 and 35 Hz. A gamma peak in either the motor cortex signal or the STN signal may be between 70 Hz and 80 Hz, and more particularly between 70 Hz and 75 Hz. In some examples, processor 40 may determine whether one or more biomarkers present correspond to a particular patient state (124). In some examples, the patient state may be one of dyskinesia, dystonia or tremor increase. For example, the presence of a motor cortex signal low beta biomarker, a motor cortex signal gamma biomarker, or an STN signal gamma biomarker may indicate a patient is experiencing dyskinesia. The dyskinesia may indicate that the patient is receiving too much treatment. Over-treatment may come in the form of too much stimulation at a particular frequency, or the current drug concentration being above the therapeutic window. For example, the amplitude or pulse width of the stimulation may be too high. The presence of a low beta peak in the STN signal may indicate that the patient is experiencing dystonia or other signs of under treatment. The lack of a high beta peak in the STN signal may indicate the patient is experiencing tremors. Based on the detected biomarkers, processor 40 may titrate therapy to modulate the biomarkers that correspond to the particular patient state (126). For example, processor 40 may use one or more control policies in order reduce the presence of a motor cortex signal low beta peak, to reduce the presence of a motor cortex signal gamma peak, and to reduce the presence of an STN signal gamma peak. In some examples, the gamma peaks in the motor cortex signal and the STN signal may both be at between approximately 70 and 80 Hz. Modulation of these biomarkers to reduce their presence helps to alleviate side effects felt by the patient such as dyskinesia. Modulation may be achieved by, for example, reduction in drug dosage, or application of stimulation. In some examples, stimulation may be delivered to the STN at approximately 55-65 Hz in order to modulate biomarkers associated with dyskinesia. In some examples, stimulation may be delivered at approximately 60 Hz. In some examples, stimulation may be provided to another area of the patient's brain, such as the GPi. Processor 40 may modify a program to reduce the presence of an STN signal low beta biomarker. Modulation of the STN low beta biomarker may be achieved by, for example, an increase in drug dosage or frequency, or application of stimulation. In some examples, stimulation may be applied at between approximately 130 Hz and 140 Hz to modulate the STN signal low beta biomarker. If the STN signal does not display a peak in the high beta range (25-35 Hz), processor 40 may provide stimulation at approximately 60 Hz to increase the presence of a high beta STN signal peak. In some examples, the exact stimulation parameters used to modulate various biomarkers may be patient specific. In some examples, the stimulation parameters may be determined using the method of FIG. 4.

Figure 6:
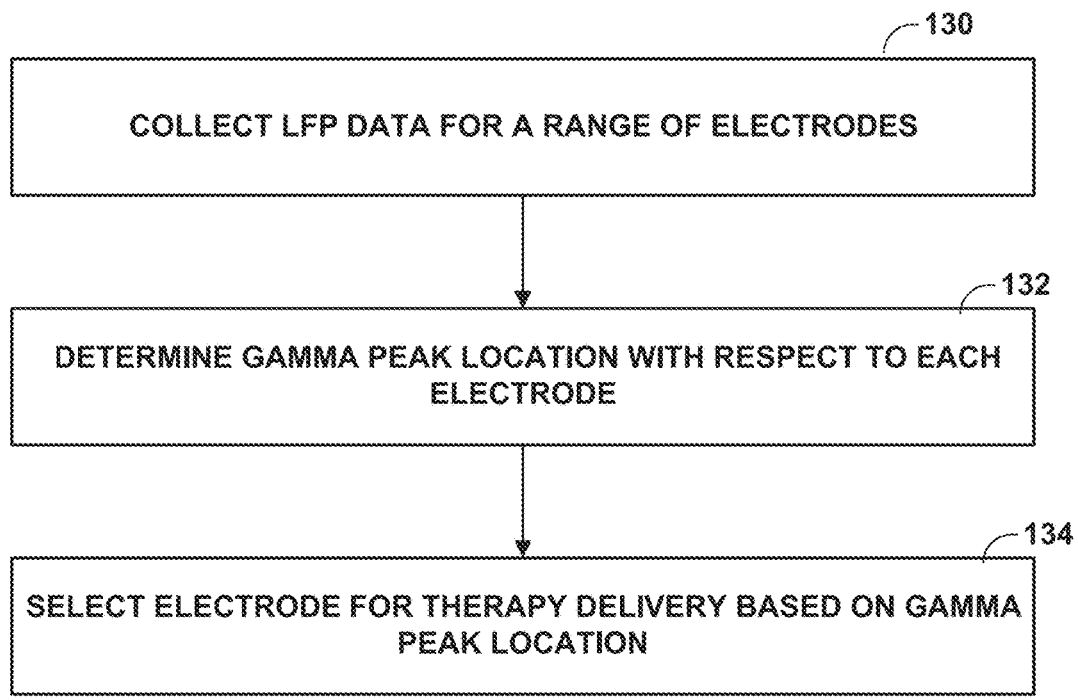
FIG. 6 is a flow chart illustrating an example method of determining the best electrodes for delivery of stimulation therapy.

FIG. 6 is a flow chart illustrating an example method of determining the best electrodes for delivery of stimulation therapy. In some examples, electrode selection may occur when a patient is in a particular patient state for which stimulation therapy is intended to correct. For example, the method of FIG. 6 may be implemented when a patient is overmedicated and exhibiting gamma peaks in a motor cortex signal and a STN signal. Although discussed with respect to gamma peaks with the motor cortex signal and the STN signal, the method may be implement using gamma peaks, beta peaks, or a combination thereof. Programmer 14 may, via IMD 16, collect LFP data from a range of electrodes (130). For example, for electrode array 24, programmer 14 may collect the LFP signal for sensed by each of electrodes 24A-24D. Based on the collected LFP signals, programmer 14 may determine gamma peak location in the collected signals with respect to each electrode (132). In addition, programmer 14 may determine which electrode senses a signal with the highest gamma peak. Programmer 14 then selects an electrode for therapy delivery based on the gamma peak location (134) within the sensed signals. In some examples, this may include selecting the electrode that sensed the highest gamma peak.

Figure 7:
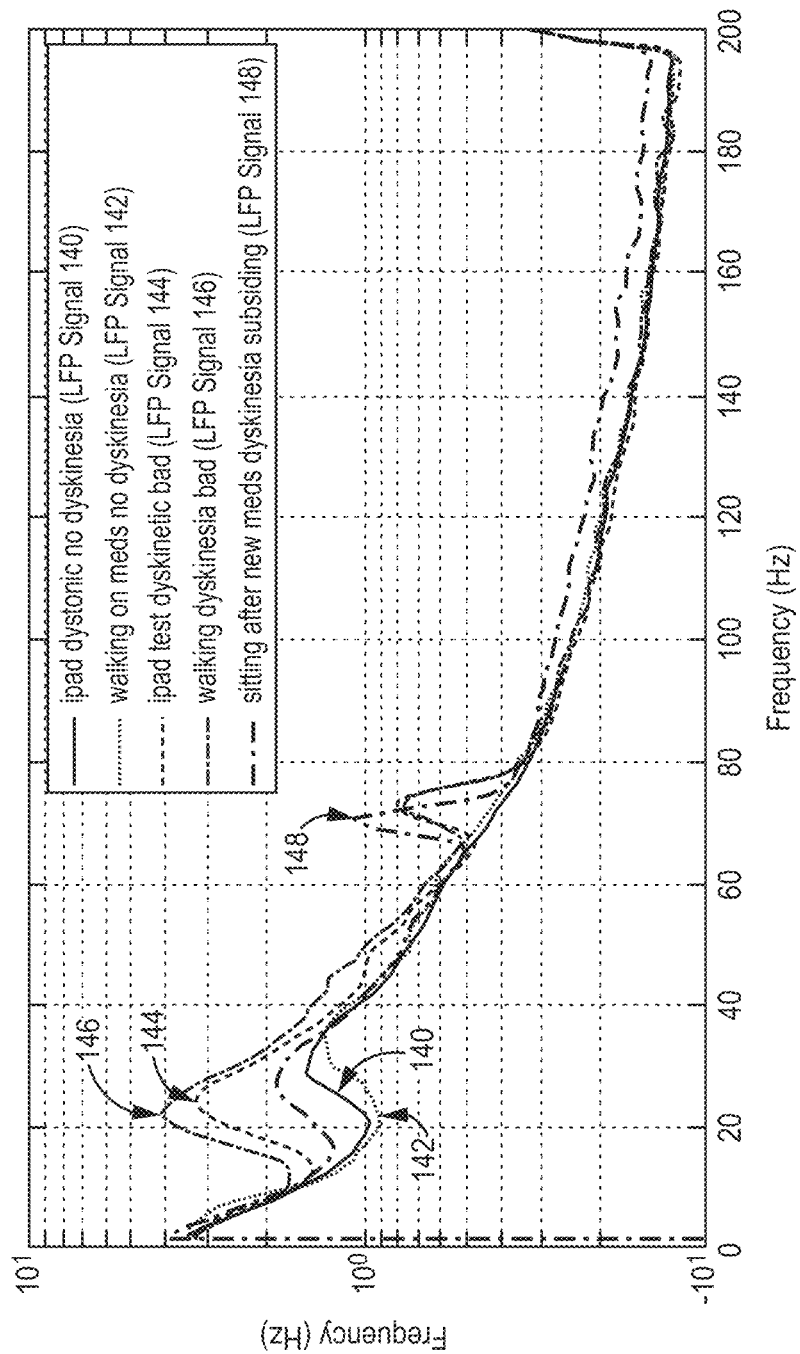
FIG. 7 is a graph illustrating LFPs sensed from a patient's motor cortex.

FIG. 7 is a graph illustrating LFPs sensed from a patient's M1. The LFP signals were collected throughout the full range of a drug dosage absorption from no medication to overmedication in a PD patient. LFP signal 140 is the LFP signal prior to a patient receiving a dose of medication intended to control PD symptoms. The patient is dystonic. As shown in FIG. 7, the LFP signal 140 includes a high beta peak amplitude at approximately 30 Hz. LFP signal 140 does not include a peak amplitude in the gamma band range. LFP signal 142 was collected while the patient is within the therapeutic window. LFP signal 142 includes a high beta peak slightly shifted towards approximately 35-40 Hz. LFP signal 142 does not include a peak in the gamma band range.

LFP signal 144 was collected when the patient was experiencing severe symptoms of over medication. These symptoms included dyskinesia. LFP signal 144 was collected while the patient was stationary. LFP signal 144 includes a low beta peak at approximately 20 Hz, and a gamma peak at approximately 75 Hz. LFP signal 146 was collected while the patient continued to experience severe symptoms of over medication, and was mobile. LFP Signal 146 includes a large low beta peak at approximately 20 Hz, and a gamma band peak at approximately 75 Hz. LFP signal 148 was collected after the patient was given additional medication to help control the dyskinesia side effects. The patient's side effects have begun to subside at the time of collection of LFP signal 148. LFP signal 148 includes a high beta ban peak at approximately 30 Hz. LFP signal 148 also includes a gamma band peak. The gamma band peak has shifted to approximately 70 Hz.

FIG. 8 is a graph showing the impact on the LFP signal of the M1 from STN stimulation. The stimulation was applied when the patient was experiencing dyskinesia symptoms. LFP signal 150 is an M1 signal similar to LFP signal 146 or 148, where the patient is experiencing dyskinesia from over medication. LFP signal 150 shows two biomarkers which stimulation is intended to modulate. The biomarkers include a low beta peak at approximately 25 HZ and a gamma band peak at approximately 70 Hz. For comparison LFP signal 152 shows an M1 LFP signal where the patient is not receiving stimulation, and is not experiencing either symptoms of PD or Dyskinesia. LFP signal 152 includes a high beta peak at approximately 30 Hz, and no peak in the gamma band. LFP signal 154 was collected while constant stimulation was being applied to the patient's STN. The constant stimulation resulted in a reduction in low beta peak, and a shift in the gamma band peak from LFP signal 150. LFP signal 156 was collected in the patient's M1 while bipolar stimulation was applied to the patient's STN. In LFP signal 156 the beta peak has been shifted into the high beta range, and the amplitude of the peak has been reduced. LFP signal 156 includes a gamma band peak that has been greatly reduced in amplitude, and has been shifted to approximately 80 Hz.

FIG. 9 is a graph showing LFP signals collected from a patient's STN. As with FIG. 7, the different LFP signals collected from the STN where sensed while a patient passed through a variety of patient states from pre-medication to over medication, and the subsiding of over-medication side effects as the medication leaves the patient's blood stream. LFP signal 160 was collected while the patient was exhibiting PD symptoms, prior to receiving medication. LFP signal 160 includes a low beta peak at approximately 22 Hz. LFP signal 160 does not appear to include a peak in the gamma band range. LFP signal 162 was collected while the patient was walking and was within the therapeutic window of the medication. LFP signal 162 includes a beta peak that has been shifted slightly to a higher frequency and does not appear to include a peak within the gamma band. LFP signal 164 was collected when the patient began to feel symptoms of dyskinesia. LFP signal 164 includes a peak at approximately 40 Hz and a small gamma peak at approximately 75 Hz. LFP signal 166 was collected while the patient was experiencing symptoms of dyskinesia while walking. LFP signal 166 is substantially similar to LFP signal 164. LFP signal 166 also includes a peak around approximately 40 Hz and a small peak within the gamma band at approximately 75 Hz. LFP signal 168 was collected while the patient was seated, and while the symptoms of overmedication were subsiding. LFP signal 168 includes a gamma band peak that has shifted to approximately 70 Hz from LFP signals 166 and 164. In addition, LFP signal 168 includes a broad peak from approximately 30 Hz to approximately 40 Hz.

FIG. 10 is a graph showing an LFP signal collected over time while electrical stimulation is provided to a patient. The signal was collected in the patient's STN. Stimulation therapy was provided to the patient's STN. At time point 170 a baseline LFP is collected from the patient while the patient is not receiving treatment for his PD symptoms. As shown at time point 170, a biomarker is observed at approximately 25 Hz, in the beta band. The patient is displaying bradykinesia. At time point 172, a sync pulse is delivered to the patient in order to align internal and external clocks. For example, a pulse with characteristics known to both the IMD and the programmer may be delivered in order to adjust and calibrate the measurements between the two devices. At time point 174 a 1V stimulation pulse is delivered at 140 Hz. The stimulation pulse results in a modest improvement to patient symptoms, and decreases the presence of the biomarker in the beta band. At time point 176, a 2 V, 140 Hz stimulation pulse is delivered. The delivery of this stimulation pulse results in the suppression of the patient's symptoms. The biomarker in the beta band disappears from the LFP. At time point 178, a 3V, 140 Hz pulse is delivered. This pulse is overstimulation, and while the biomarker in the beta band is suppressed, a biomarker appears in the gamma band. At time point 180 stimulation was turned off. The beta band biomarker reappears, along with the patient's symptoms. In addition the biomarker in the gamma band is no longer present.

Based on the information contained in FIGS. 8-10, programmer 14, may create an algorithm by which to provide stimulation alone or in combination with medication in order to maintain a patient within the patient's therapeutic window. For example, a patient specific algorithm may include providing stimulation at 2V and 140 Hz in response to the presence of activity in the beta band in an LFP signal sensed in the STN.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various examples consistent with this disclosure have been described. These and other examples are within the scope of the following claims.

What is claimed is:

1. A method comprising:
   acquiring, with a medical device, a plurality of electrical signals from a brain of a patient being treated for a movement disorder with a medication and electrical stimulation, wherein at least one electrical signal of the plurality of electrical signals is acquired from a motor cortex of the brain and at least one electrical signal of the plurality of electrical signals is acquired from a subthalamic nucleus (STN) of the brain;
   determining whether at least a first predetermined biomarker is present in a first set of electrical signals of the plurality of electrical signals, the first predetermined biomarker associated with at least one of the patient being over-treated or the presence of side effects of the medication;
   determining whether at least a second predetermined biomarker is present in a second set of electrical signals of the plurality of electrical signals, the second predetermined biomarker associated with at least one of the patient being under-treated or the presence of movement disorder symptoms, the second set of electrical signals comprising the at least one electrical signal acquired from the STN, the second predetermined biomarker comprises a low beta band peak in the at least one electrical signal acquired from the STN, wherein the first set of electrical signals is not identical to the second set of electrical signals; and
   titrating, based on whether or not the first predetermined biomarker is present and whether or not the second predetermined biomarker is present, at least one therapy parameter of the electrical stimulation to maintain the patient within a therapeutic window in which movement disorder symptoms and side effects of the medication are reduced.

2. The method of claim 1, wherein titrating the at least one therapy parameter comprises adjusting a frequency of electrical stimulation.

3. The method of claim 2, wherein adjusting a frequency of electrical stimulation comprises adjusting the frequency to at least one of: a frequency of the first predetermined biomarker based on the first predetermined biomarker being present; a frequency of the second predetermined biomarker based on the second predetermined biomarker being present; approximately 55-65 Hz; or approximately 120-140 Hz.

4. The method of claim 2, wherein the method further comprises delivering electrical stimulation to a patient at the adjusted frequency.

5. The method of claim 4, further comprising delivering electrical simulation to the STN of the brain of the patient at the adjusted frequency.

6. The method of claim 1, wherein titrating at least one therapy parameter comprises delivering electrical stimulation at alternating frequencies.

7. The method of claim 6, wherein delivering electrical stimulation at alternating frequencies comprises delivering electrical stimulation alternating between frequencies of approximately 55-65 Hz and approximately 120-140 Hz.

8. The method of claim 1, wherein the first set of electrical signals comprises a the at least one electrical signal acquired from the motor cortex of the brain of the patient.

9. The method of claim 1, wherein titrating the at least one therapy parameter comprises titrating the at least one therapy parameter at a first time, and the method further comprising:
   acquiring, after the first time, an updated first set of electrical signals;
   acquiring, after the first time, an updated second set of electrical signals;
   determining whether at least the first predetermined biomarker is present in the updated first set of electrical signals;
   determining whether at least the second predetermined biomarker is present in the updated second set of electrical signals;
   analyzing the efficacy of the titrated therapy parameter based on whether the first predetermined biomarker is present in the updated first set of electrical signals or second predetermined biomarker is present in the updated second set of electrical signals; and
   re-titrating the at least one therapy parameter based on the efficacy of the titrated at least one therapy parameter.

10. The method of claim 1, wherein the first predetermined biomarker and the second predetermined biomarker are patient specific.

11. The method of claim 10, further comprising:
    identifying, based on electrical signals acquired from the brain of the patient, the first predetermined biomarker and the second predetermined biomarker.

12. A system comprising:
    an implantable medical device comprising a memory and a processor; and
    a plurality of electrodes in communication with the implantable medical device, the plurality of electrodes configured to be implanted in a brain of a patient being treated for a movement disorder with a medication and electrical stimulation;
    wherein the processor is configured to:
      acquire, via the plurality of electrodes, a plurality of electrical signals, wherein at least one electrical signal of the plurality of electrical signals is acquired from a motor cortex of the brain and at least one electrical signal of the plurality of electrical signals is acquired from a subthalamic nucleus (STN) of the brain;
      determine whether at least a first predetermined biomarker is present in a first set of electrical signals of the plurality of electrical signals, the first predetermined biomarker associated with at least one of the patient being over-treated or the presence of side effects of the medication;
      determine whether at least a second predetermined biomarker is present a second set of electrical signals of the plurality of electrical signals, the second predetermined biomarker associated with at least one of the patient being under-treated or the presence of movement disorder symptoms, the second set of electrical signals comprising the at least one electrical signal acquired from the STN, the second predetermined biomarker comprises a low beta band peak in the at least one electrical signal acquired from the STN, wherein the first set of electrical signals is not identical to the second set of electrical signals; and
      titrate, based on whether or not the first predetermined biomarker is present and whether or not the second predetermined biomarker is present, at least one therapy parameter of the electrical stimulation to maintain the patient within a therapeutic window in which movement disorder symptoms and side effects of the medication are reduced.

13. The system of claim 12, wherein, to titrate the at least one therapy parameter, the processor is further configured to adjust a frequency of electrical stimulation.

14. The system of claim 13, wherein, to adjust the frequency of the electrical stimulation, the processors is configured to adjust the frequency of the electrical stimulation to alternate between frequencies of approximately 55-65 Hz and approximately 120-140 Hz.

15. The system of claim 13, wherein the processor is further configured to adjust the frequency to at least one of: a frequency of the first predetermined biomarker based on the first predetermined biomarker being present; a frequency of the second predetermined biomarker based on the second predetermined biomarker being present; approximately 55-65 Hz; or approximately 120-140 Hz.

16. The system of claim 13, further comprising a stimulation generator configured to deliver electrical stimulation to the patient at the adjusted frequency.

17. The system of claim 16, wherein the stimulation generator is configured to deliver the electrical stimulation to the STN of the brain of the patient at the adjusted frequency via one or more of the plurality of electrodes.

18. The system of claim 12, wherein, to titrate the at least one therapy parameter, the processor is configured to cause the implantable medical device to deliver electrical stimulation at alternating frequencies.

19. The system of claim 12, wherein the first set of electrical signals comprises the at least one electrical signal from the motor cortex of the brain of the patient.

20. The system of claim 12, wherein, to titrate the at least one therapy parameter, the processor is configured to titrate the at least one therapy parameter at a first time, wherein the processor is further configured to:
- acquire, after the first time, an updated first set of electrical signals;
- acquire, after the first time, an updated second set of electrical signals;
- determine whether at least the first predetermined biomarker is present in the updated first set of electrical signals;
- determine whether at least the second predetermined biomarker is present in the updated second set of electrical signals;
- analyze the efficacy of the adjusted therapy parameter based on whether or not the first predetermined biomarker is present in the updated first set of electrical signals and whether or not the second predetermined biomarker is present in the updated second set of electrical signals; and
- re-titrate the at least one therapy parameter based on the efficacy of the titrated at least one therapy parameter.

21. A system comprising:

means for acquiring, with a medical device, a plurality of electrical signals from a brain of a patient being treated for a movement disorder with a medication and electrical stimulation, wherein at least one electrical signal of the plurality of electrical signals is acquired from a motor cortex of the brain and at least one electrical signal of the plurality of electrical signals is acquired from a subthalamic nucleus (STN) of the brain;

means for determining whether at least a first predetermined biomarker is present in a first set of electrical signals of the plurality of electrical signals, the first predetermined biomarker associated with at least one of the patient being over-treated or the presence of side effects of the medication;

means for determining whether at least a second predetermined biomarker is present in a second set of electrical signals of the plurality of electrical signals, the second predetermined biomarker associated with at least one of the patient being under-treated or the presence of movement disorder symptoms, the second set of electrical signals comprising the at least one electrical signal acquired from the STN, the second predetermined biomarker comprises a low beta band peak in the at least one electrical signal acquired from the STN, wherein the first set of electrical signals is not identical to the second set of electrical signals; and means for titrating, based on whether or not the first predetermined biomarker is present and whether or not the second predetermined biomarker is present, at least one therapy parameter of the electrical stimulation to maintain the patient within a therapeutic window in which movement disorder symptoms and side effects of the medication are reduced.

* * * * *